United States Patent
Husar et al.

(10) Patent No.: US 7,054,681 B2
(45) Date of Patent: May 30, 2006

(54) DEVICE AND METHOD FOR CARRYING OUT SPATIALLY DIRECTED DETECTION OF AN ELECTROENCEPHALOGRAM

(75) Inventors: Peter Husar, Ilmenau (DE); Gunter Henning, Ilmenau (DE); Klaus Schellhorn, Ilmenau (DE); Sebastian Berkes, Ilmenau (DE); Falk Schlegelmilch, Ilmenau (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/169,816

(22) PCT Filed: Nov. 21, 2001

(86) PCT No.: PCT/EP01/13476

§ 371 (c)(1),
(2), (4) Date: Nov. 12, 2002

(87) PCT Pub. No.: WO02/41774

PCT Pub. Date: May 30, 2002

(65) Prior Publication Data

US 2004/0068198 A9    Apr. 8, 2004

(30) Foreign Application Priority Data

Sep. 14, 2001  (DE) ............... 101 45 325

(51) Int. Cl.
*A61B 5/04* (2006.01)
(52) U.S. Cl. ............ 600/544; 600/382; 600/383
(58) Field of Classification Search ........ 600/544–547, 600/554, 372, 382, 383, 386, 390, 393
See application file for complete search history.

(56) References Cited

U.S. PATENT DOCUMENTS

| | | | | |
|---|---|---|---|---|
| 3,807,387 A | * | 4/1974 | MacNichol, Jr. | 600/544 |
| 4,817,627 A | * | 4/1989 | Cohen et al. | 600/544 |
| 4,907,597 A | * | 3/1990 | Chamoun | 600/544 |
| 5,291,888 A | * | 3/1994 | Tucker | 600/383 |
| 5,357,957 A | * | 10/1994 | Itil et al. | 600/383 |
| 5,564,433 A | * | 10/1996 | Thornton | 600/544 |
| 6,073,039 A | * | 6/2000 | Berson | 600/372 |
| 6,122,544 A | * | 9/2000 | Organ | 600/547 |
| 6,574,513 B1 | * | 6/2003 | Collura et al. | 607/122 |
| 6,745,062 B1 | * | 6/2004 | Finneran et al. | 600/393 |

FOREIGN PATENT DOCUMENTS

| WO | WO 99/22642 | 5/1999 |
|---|---|---|
| WO | WO 99/23942 | 5/1999 |
| WO | WO 99/38437 | 8/1999 |

OTHER PUBLICATIONS

International Search Report.

* cited by examiner

*Primary Examiner*—Charles Marmor
(74) *Attorney, Agent, or Firm*—Patterson, Thuente, Skaar & Christensen, P.A.

(57) ABSTRACT

A method and arrangement for acquiring an electroencephalogram (EEG) are disclosed. A first set of electrodes is arranged to sense cortical signals generated primarily in a region of interest (ROI). A second set of electrodes are arranged to sense cortical signals generated inside and outside of the ROI. Individual signals sensed by each electrode of the first and second sets of electrodes are directed to a signal analyzer.

9 Claims, 1 Drawing Sheet

DEVICE AND METHOD FOR CARRYING OUT SPATIALLY DIRECTED DETECTION OF AN ELECTROENCEPHALOGRAM

PRIORITY BASED ON FOREIGN FILING

This Application claims priority based on the following patent applications filed in Germany: Application No. 100 58 128.5, having a priority date of Nov. 22, 2000; and Application No. 10145325.6, having a priority date of Sep. 14, 2001.

FIELD OF THE INVENTION

The invention relates generally to medical measurement and diagnostics, and more particularly, to measuring cortical signals generated in a particular region of interest.

BACKGROUND OF THE INVENTION

The latest technology knows systems that capture the EEG with suitable electrodes at predefined standardized positions and feed it to an amplifier. The disadvantageous effect is that the electrical activity can only be captured from relatively large areas of the brain.

But in many medical problems of neurology, physiology or the function diagnostic the local brain activity of certain anatomical limited areas or centers is of more essential significance. A series of extensive signal processing steps is necessary to capture the electrical activity of such areas and to free them from disturbances by the adjacent brain areas. For that the amplified EEG must be digitalized and afterwards analyzed in a computer.

One disadvantage of this procedure is that only an offline analysis is possible. Therefore, this procedure can not be used in time critical procedures either.

SUMMARY OF THE INVENTION

One aspect of the invention is to supply a procedure and an arrangement in which the local electrical activity of a spatial limited brain area is captured and can be used for further processing and/or analysis. At the same time the affecting and disrupting fields from the adjacent brain areas on the desired area to be examined shall be considerably suppressed in their projection on the deviated potential.

According to one embodiment of the invention, it is intended with an arrangement for the spatial directed capturing of an electro encephalogram, in which electrodes are attached to the skull surface of the examined person, that parts of the electrodes are arranged in such a way that they capture the activity of the targeted cortical structure, and other parts of the electrodes are arranged in such a way that they capture the activity of the targeted cortical structure and the activity of the surrounding areas and furthermore an electronic evaluation circuit exists.

In an advantageous advancement of the arrangement according to one embodiment of the invention, the electrodes are axial symmetrically arranged around a reference electrode in an inner ring and an outer ring.

Another aspect of the invention concerns a procedure for the spatial directed capturing of the electro encephalogram, in which the electrical activity is measured over the targeted cortical structure as well as over the targeted cortical structure and the adjacent area and the received potentials are amplified and feed to an electrical circuit.

In an advantageous advancement of the procedure according to one embodiment of the invention, it is intended that the spatial directional pattern for the capturing of the activity of a targeted cortical structure is realized with signal processing algorithms.

The arrangement on hand, according to the invention, and the procedure belonging to it is characterized in a way that the electrical activity of the targeted brain area is freed from disturbances simultaneously to the EEG capturing. In traditional capturing methods this is only possible with the help of offline analysis, meaning with methods of signal processing that are based on several repetitions of the measurement and are therefore clinically realized in a lot of cases with unacceptable delays.

DETAILED DESCRIPTION

Figure 1:
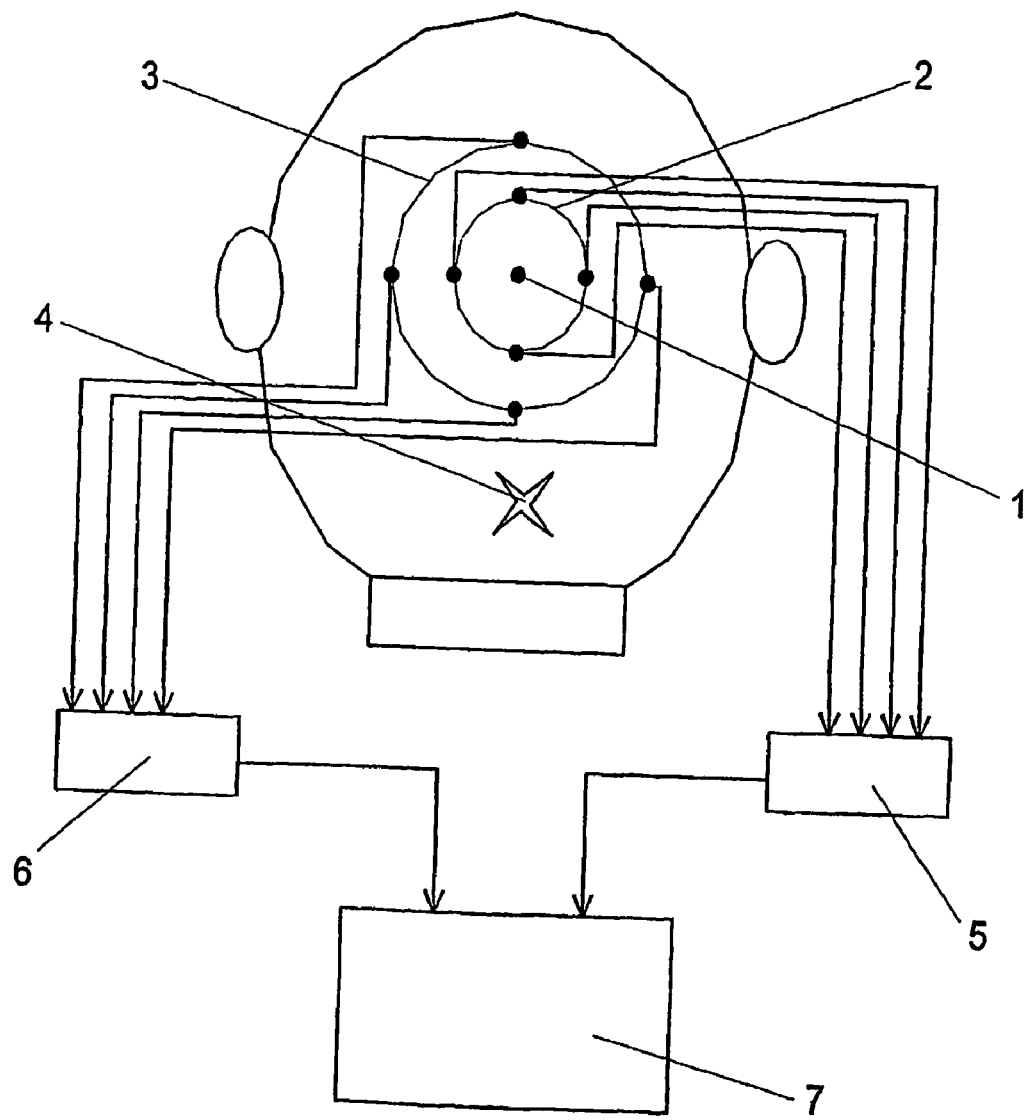
FIG. 1 illustrates an EEG measurement arrangement according to one embodiment of the present invention.

The arrangement illustrated in FIG. 1 can be used for examination of the visual cortex. A double ring-shaped electrode pattern is attached on the skull surface over the visual cortex of the patient above the inion 4. The number of the used electrodes depends on the respective technical equipment. They are axial symmetrically arranged around the reference electrode 1.

The electrodes of the inner electrode ring 2 are positioned directly above the ROI (region of interest—the target area). Its measurements have to be selected depending on the known anatomical characteristics.

The electrodes of the outer electrode ring 3 additionally cover the activity of the areas surrounding the ROI. The electrode potentials of the inner ring 2 and the outer ring 3 are amplified with common EEG amplifiers 5 and 6 and fed to the electronic block 7. The electrical direction pattern of the electrode configuration and the interference suppression of adjacent brain areas is realized with a suitable analog and digital circuit technology as well as with an algorithm implemented in a micro controller or signal processor. The formed difference of the activities of both brain volumes creates an almost undisturbed activity of the examined area (ROI). The examined person can already receive diagnostically relevant information during the reception of the brain potentials.

What is claimed is:

1. A method of acquiring an electroencephalogram (EEG), the method comprising:

attaching a first set of electrodes to a patient's head such that electrodes of the first set are arranged to sense cortical signals generated primarily in a region of interest (ROI);

attaching a second set of electrodes to the patient's head such that electrodes of the second set are arranged to sense cortical signals generated inside and outside of the ROI;

attaching at least one reference electrode to the patient's head, wherein the electrodes of the first set are arranged symmetrically about the reference electrode, and the electrodes of the second set are arranged symmetrically about the reference electrode; and directing individual signals sensed by each electrode of the first and second sets of electrodes to a signal analyzer.

2. The method of claim 1, wherein when the electrodes of the first and second sets are attached, the electrodes of the second set are arranged around the electrodes of the first set.

3. The method of claim 1, wherein when the electrodes of the first and second sets are attached, the electrodes of the second set are arranged symmetrically about the electrodes of the first set.

4. The method of claim 3, wherein the electrodes of the first set are arranged in a pattern along a reference inner ring and the electrodes of the second set are arranged in a pattern along a reference outer ring that is concentric with the reference inner ring.

5. The method of claim 1, and further comprising:

processing each of the individual electrical signals to produce an EEG based primarily on signals generated in the ROI.

6. The method of claim 5, wherein the processing is performed by the signal analyzer.

7. The method of claim 5, wherein the processing includes implementing a signal processing algorithm.

8. The method of claim 5, wherein the processing includes suppressing an BEG component that is caused by signals generated outside of the ROI.

9. The method of claim 8, further comprising:

sensing cortical signals with the first and second sets of electrodes;

wherein the processing is performed during the sensing.

* * * * *

UNITED STATES PATENT AND TRADEMARK OFFICE
CERTIFICATE OF CORRECTION

PATENT NO. : 7,054,681 B2  
APPLICATION NO. : 10/169816  
DATED : May 30, 2006  
INVENTOR(S) : Peter Husar et al.

Page 1 of 1

It is certified that error appears in the above-identified patent and that said Letters Patent is hereby corrected as shown below:

On Title Page
Under (75) Inventors:

Delete "Gunter" and insert --Guenter--

Signed and Sealed this

Twentieth Day of February, 2007

JON W. DUDAS  
*Director of the United States Patent and Trademark Office*